United States Patent
Lee et al.

(10) Patent No.: US 10,219,968 B2
(45) Date of Patent: Mar. 5, 2019

(54) JOINT ASSEMBLY AND WALKING ASSISTANT ROBOT HAVING THE SAME

(71) Applicant: Samsung Electronics Co., Ltd., Suwon-Si, Gyeonggi-Do (KR)

(72) Inventors: Jong Won Lee, Uiwang-si (KR); Yong Jae Kim, Seoul (KR); Young Do Kwon, Yongin-si (KR); Jeong Hun Kim, Hwaseong-si (KR); Youn Baek Lee, Yongin-si (KR); Se Gon Roh, Suwon-si (KR); Min Hyung Lee, Anyang-si (KR); Byung June Choi, Gunpo-si (KR); Hyun Do Choi, Yongin-si (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 281 days.

(21) Appl. No.: 14/592,694

(22) Filed: Jan. 8, 2015

(65) Prior Publication Data
US 2015/0196450 A1 Jul. 16, 2015

(30) Foreign Application Priority Data

Jan. 16, 2014 (KR) ...................... 10-23014-0005453

(51) Int. Cl.
*A61H 3/00* (2006.01)
*A61F 5/01* (2006.01)
*A61H 1/02* (2006.01)

(52) U.S. Cl.
CPC ............. *A61H 3/00* (2013.01); *A61F 5/0102* (2013.01); *A61H 1/024* (2013.01); *A61H 1/0244* (2013.01);
(Continued)

(58) Field of Classification Search
CPC .... A61F 5/0111; A61F 5/0127; A61F 5/0102; A61F 5/0113; A61F 2005/0137; A61F 2005/0132; A61F 2005/0134; A61F 2005/0146; A61F 2005/0153; A61F 2005/0148; A61F 2/6607; A61H 3/00; A61H 3/06; A61H 3/008; A61H 1/0237; A61H 1/0266; A61H 1/02; A61H 1/024; A61H 1/0244; A61H 1/0274; A61H 1/0277; A61H 1/0285; A61H 2201/0157; A61H 2201/1269; A61H 2201/1276;
(Continued)

(56) References Cited

U.S. PATENT DOCUMENTS 6,358,190 B1 * 3/2002 Pellis .................... A61F 5/0123
482/136
6,821,259 B2 * 11/2004 Rahman ............... A61F 5/0102
601/24
(Continued)

FOREIGN PATENT DOCUMENTS

JP 2010110465 A 5/2010
KR 20130024061 A 3/2013

*Primary Examiner* — Keri J Nelson
*Assistant Examiner* — Adam Baker
(74) *Attorney, Agent, or Firm* — Harness, Dickey & Pierce, P.L.C.

(57) ABSTRACT

According to an aspect of the present invention, it is possible to implement a joint assembly operating similar to a user's actual ankle joint. An ankle joint included in a walking assistant robot is pivotable around a rotation axis located outside the ankle joint.

9 Claims, 12 Drawing Sheets

(52) U.S. Cl.
CPC ... *A61H 1/0266* (2013.01); *A61H 2201/0192* (2013.01); *A61H 2201/164* (2013.01); *A61H 2201/165* (2013.01); *A61H 2201/1628* (2013.01); *A61H 2201/5061* (2013.01); *Y10S 901/28* (2013.01)

(58) Field of Classification Search
CPC .... A61H 2201/1676; A61H 2203/0406; A61H 2205/12; A61H 2205/106; A61H 2205/10; A61H 2205/108
USPC ....... 602/16, 27–29; 623/47–52; 601/23, 27, 601/33, 34, 29, 31, 32
See application file for complete search history.

(56) References Cited

U.S. PATENT DOCUMENTS

| | | |
|---|---|---|
| 7,628,766 B1 | 12/2009 | Kazerooni et al. |
| 2006/0276728 A1* | 12/2006 | Ashihara ............... A61F 5/0102 601/5 |
| 2008/0304935 A1* | 12/2008 | Scott ................... A61B 5/1038 414/5 |
| 2010/0036302 A1* | 2/2010 | Shimada ............... A61F 5/0102 602/16 |
| 2010/0207354 A1 | 8/2010 | Hunziker |
| 2010/0210980 A1* | 8/2010 | Kudoh .................. A61H 3/008 601/34 |

* cited by examiner

JOINT ASSEMBLY AND WALKING ASSISTANT ROBOT HAVING THE SAME

CROSS-REFERENCE TO RELATED APPLICATION

This application claims the benefit of Korean Patent Application No. P2014-5453, filed on Jan. 16, 2014 in the Korean Intellectual Property Office, the entire disclosure of which is incorporated herein by reference.

BACKGROUND

1. Field

Example embodiments relate to a joint assembly and a walking assistant robot having the same. In some example embodiments, the joint assembly is configured to support a load and be pivotable having the same rotation center.

2. Description of the Related Art

Depending on the field of usage, walking assistant robots may be used as an assistant device for aiding a user having a decreased muscular strength and a body weight, or as a power assist robot for amplifying the user's muscular strength and supporting a load of a heavy object instead of the user for, for example, carrying the heavy object.

SUMMARY

Some example embodiments are related to a joint assembly capable of performing an operation similar to a user's ankle joint, and a walking assistant robot having the same.

According to some example embodiments, the joint assembly is configured to connect a frame and a foot structure which are mounted on a user's body.

In some example embodiments, the joint assembly may include a first joint unit configured to enable the foot structure to be pivoted with respect to the frame in a first direction, and a second joint unit configured to enable the foot structure to be pivoted with respect to the frame in a second direction.

The first joint unit may be pivoted in the first direction such that a toe of the user wearing the foot structure faces upward or downward (plantar-flexion/dorsi-flexion).

The second joint unit may be pivoted in the second direction such that a foot of the user wearing the foot structure is pivoted in a horizontal direction (inversion/eversion).

The second joint unit may include a first link unit including a first link pivotably connected to the frame side and a second link in which one side is pivotably connected to the first link and the other side is pivotably connected to the foot structure, a second link unit including a third link that is located parallel to the first link and is pivotably connected to the frame side and a fourth link located parallel to the second link and in which one side is pivotably connected to the third link and the other side is pivotably connected to the foot structure side, and an assistant link configured to constantly maintain a distance between the first link unit and the second link unit.

The assistant link may include a first assistant link connecting the first link and the second link unit and a second assistant link connecting the second link and the second link unit.

In the first assistant link, one side may be mounted on a link axis provided between one end and the other end of the first link, and the other side may be mounted on a link axis connecting the third link and the fourth link.

In the second assistant link, one side may be mounted on a link axis provided between one end and the other end of the second link, and the other side may be mounted on a link axis connecting the third link and the fourth link.

A distance between a link axis connecting the first link and the frame side and a link axis connecting the first link and the first assistant link may be the same as a distance between a link axis connecting the third link and the frame side and a link axis connecting the third link and the fourth link.

A distance between a link axis connecting the second assistant link and the second link and a link axis connecting the second link and the foot structure side may be the same as a distance between a link axis connecting the third link and the fourth link and a link axis connecting the fourth link and the foot structure side.

The first link unit and the second link unit may be pivoted around the same rotation axis located outside the joint assembly.

The first link, the first assistant link, and the third link may have a shape of a parallelogram.

The second link, the second assistant link, and the fourth link may have a shape of a parallelogram.

The joint assembly may further include a first joint unit provided in the frame and a second joint unit pivotably connected to the first joint unit.

The first link unit and the second link unit may be pivotably connected to the second joint unit.

The second joint unit may be pivotable in the first direction and the first link unit and the second link unit may be pivotable in the second direction.

The first link unit and the second link unit may be pivotably connected to a connecting joint unit, and the connecting joint unit may be mounted on the foot structure.

The foot structure may include a connecting unit on which the connecting joint unit is mounted.

The connecting unit and the connecting joint unit may be connected to move up or down.

According to other example embodiments, a walking assistant robot may be mounted on a user's body and aid walking of the user.

In some example embodiments, the robot may include a frame mounted on the user's leg, a foot structure mounted on the user's foot, and an ankle joint having two degrees of freedom and configured to connect the foot structure to the frame to be pivotable in a first direction or a second direction, wherein, when the foot structure is pivoted in the second direction, a pivot center is located outside the ankle joint.

The ankle joint may include a first joint unit mounted on the frame, a second joint unit connected to the first joint unit to be pivotable in the first direction, and a third joint unit connected to the second joint unit to be pivotable in the second direction, and the third joint unit may include a first link unit, a second link unit located parallel to the first link unit, and an assistant link configured to constantly maintain a distance between the first link unit and the second link unit.

The first link unit may include a first link connected to the second joint unit and a second link pivotably connected to the first link and configured to connect the first link and the foot structure.

The second link unit may include a third link that is connected to the second joint unit and is parallel to the first link, and a fourth link that is pivotably connected to the third link, connects the third link and the foot structure, and is parallel to the second link.

The assistant link may include a first assistant link connecting the first link and the second link unit, and a second assistant link connecting the second link and the second link unit.

The third joint unit may be pivoted around a rotation axis located outside the ankle joint in the second direction.

According to still another aspect of the present invention, there is provided a walking assistant robot that is mounted on a user's body and aids walking of the user. The robot includes a frame mounted on the user's body; a foot structure mounted on the user's foot; and an ankle joint pivotably connecting the frame and the foot structure, wherein the ankle joint includes: a first joint unit mounted on the frame; a second joint unit that is mounted on the first joint unit by a rotation axis and is pivotable around the rotation axis; and a third joint unit mounted on the second joint unit to be pivotable around a rotation axis located outside the ankle joint, and wherein the second joint unit is pivoted to correspond to a pivot operation of the user's ankle in a first direction, and the third joint unit is pivoted to correspond to a pivot operation of the user's ankle in a second direction.

The third joint unit may include a first link unit connected to the second joint unit, a second link unit located parallel to the first link unit, and an assistant link configured to constantly maintain a distance between the first link unit and the second link unit.

The first link unit may include a first link and a second link pivotably connected to the first link, and the second link unit may include a third link and a fourth link pivotably connected to the third link by a link axis.

The assistant link may include a first assistant link connecting between the first link and a link axis connecting the third link and the fourth link, and a second assistant link connecting between the second link and a link axis connecting the third link and the fourth link.

When the ankle joint is pivoted in the second direction, the first link and the third link may be located in parallel and pivoted by the first assistant link, and the second link and the fourth link may be located in parallel and pivoted by the second assistant link.

The foot structure may be pivoted in the first direction such that a toe of the user wearing the foot structure faces upward or downward (plantar-flexion/dorsi-flexion).

The foot structure may be pivoted in the second direction such that a foot of the user wearing the foot structure is pivoted in a horizontal direction (inversion/eversion).

BRIEF DESCRIPTION OF THE DRAWINGS

These and/or other aspects of the example embodiments will become apparent and more readily appreciated from the following description of some of the example embodiments, taken in conjunction with the accompanying drawings of which.

DETAILED DESCRIPTION

Figure 1:
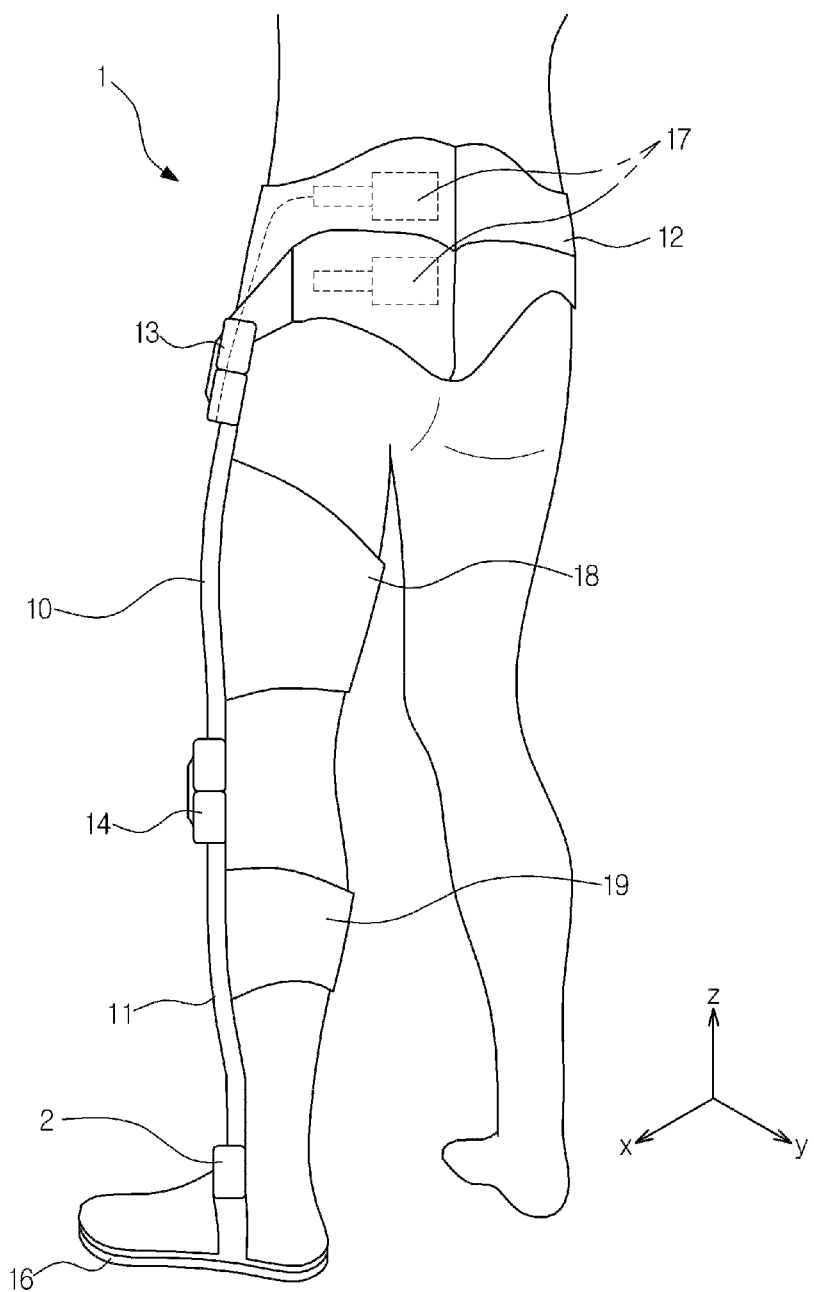
FIG. 1 is a conceptual diagram illustrating a walking assistant robot according to some example embodiments.

Hereinafter, a joint assembly according to some example embodiment and a walking assistant robot having the same will be described in detail with reference to the drawings.

In the drawings, the thicknesses of layers and regions are exaggerated for clarity. Like reference numerals in the drawings denote like elements.

Detailed illustrative embodiments are disclosed herein. However, specific structural and functional details disclosed herein are merely representative for purposes of describing example embodiments. Example embodiments may be embodied in many alternate forms and should not be construed as limited to only those set forth herein.

It should be understood, however, that there is no intent to limit this disclosure to the particular example embodiments disclosed. On the contrary, example embodiments are to cover all modifications, equivalents, and alternatives falling within the scope of the example embodiments. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of this disclosure. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting. As used herein, the singular forms "a," "an," and "the," are intended to include the plural forms as well, unless the context clearly indicates otherwise. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Various example embodiments will now be described more fully with reference to the accompanying drawings in which some example embodiments are shown. In the drawings, the thicknesses of layers and regions are exaggerated for clarity.

FIG. 1 is a conceptual diagram illustrating a walking assistant robot according to some example embodiments.

As illustrated in FIG. 1, a walking assistant robot 1 may include frames 10 and 11 extending in a length direction of a user's leg. The frames 10 and 11 may include a first frame 10 and a second frame 11. The walking assistant robot 1 may include a foot structure 16 mounted on the user's foot.

The first frame 10 and a waist fixing device 12 may be connected by a hip joint 13 of the walking assistant robot 1. The first frame 10 and the second frame 11 may be connected by a knee joint 14 of the walking assistant robot 1. The second frame 11 and the foot structure 16 may be connected by an ankle joint 2 of the walking assistant robot 1.

The walking assistant robot 1 may further include a driving source 17 and fixing devices 18 and 19. The driving source 17 provides driving force to the hip joint 13 and the knee joint 14. The fixing devices 18 and 19 may mount the frames 10 and 11 on the user's body.

The first frame 10 may be affixed to the user's femoral region and the second frame 11 may be affixed to the user's calf. The hip joint 13 pivotably connects the first frame 10 to the waist fixing device 12. The knee joint 14 pivotably connects the second frame 11 to the first frame 10. The ankle joint 2 pivotably connects the foot structure 16 to the second frame 11.

The first frame 10 may be configured to support the user's femoral region and the second frame 11 may be configured to support the user's calf. The first frame 10 and the second frame 11 may be pivotably connected by the knee joint 14. In the first frame 10, the first fixing device 18 configured to fix the first frame 10 in the user's femoral region may be connected to the knee joint 14. In the second frame 11, the second fixing device 19 configured to fix the second frame 11 in the user's calf may be connected to the knee joint 14.

The first fixing device 18 and the second fixing device 19 may be provided in the form of a fastener. The frames 10 and 11 may come in close contact with the user's leg and be fixed thereto by the first fixing device 18 and the second fixing device 19. The first fixing device 18 and the second fixing device 19 may be adjusted to match a size of the user's leg.

The first frame 10 may be connected with the waist fixing device 12 by the hip joint 13. The waist fixing device 12 may be made of a strap that has flexibility to be adjusted to match the user's waist circumference. For example, the waist fixing device 12 may be a hook and loop fastener such as Velcro, or a strap including a fixing unit such as a buckle, a ratchet buckle, or a catch.

The hip joint 13 may have three degrees of freedom (DOFs). The first frame 10 connected to the hip joint 13 may be pivoted around an x axis, a y axis, and a z axis.

The first frame 10 may be pivoted around the x axis by the hip joint 13. The hip joint 13 may receive a driving force from the driving source 17 and pivot the first frame 10 around the x axis. The first frame 10 is connected to the hip joint 13 or the waist fixing device 12 by a hinge device or the like, and may be pivoted around the y axis. To enable the first frame 10 to be pivoted around the z axis, the first frame 10 or the hip joint 13 connected to the first frame 10 may be slidably provided along the waist fixing device 12.

The second frame 11 may be connected to the foot structure 16 by the ankle joint 2. The ankle joint 2 may have three degrees of freedom (DOFs). The second frame 11 or the foot structure 16 may be pivoted around the ankle joint 2. The ankle joint 2 may support a load transmitted by the second frame 11. A pivot structure and a load support structure of the ankle joint 2 will be described in more detail below.

The foot structure 16 may fix the user's foot. In a floor surface of the foot structure 16 with which the user's foot comes in contact, a sensor may be provided. The sensor may detect a load change and the like of the user wearing the walking assistant robot 1, and may transmit the detected information to a control unit (not illustrated).

The control unit (e.g. a controller) may control an operation of the hip joint 13, the knee joint 14, and the like using the information detected by the sensor.

The control unit may include a processor and a memory (not shown).

The processor may be an arithmetic logic unit, a digital signal processor, a microcomputer, a field programmable array, a programmable logic unit, a microprocessor or any other device capable of responding to and executing instructions in a defined manner such that the processor is programmed with instructions that configure the processor as a special purpose computer to perform various the operations such as detecting a load change and the like of the user.

The first frame 10 and the second frame 11 may be pivoted around the knee joint 14. The knee joint 14 may have two degrees of freedom (DOFs). The knee joint 14 may receive the driving force from the driving source 17 and may pivot the first frame 10 or the second frame 11 with two degrees of freedom. The first frame 10 or the second frame 11 may simultaneously perform rolling and sliding operations to correspond to motion of the user's knee joint.

Hereinafter, a structure of the ankle joint 2 of the walking assistant robot 1 according to some example embodiments will be described in detail.

Figure 2A:
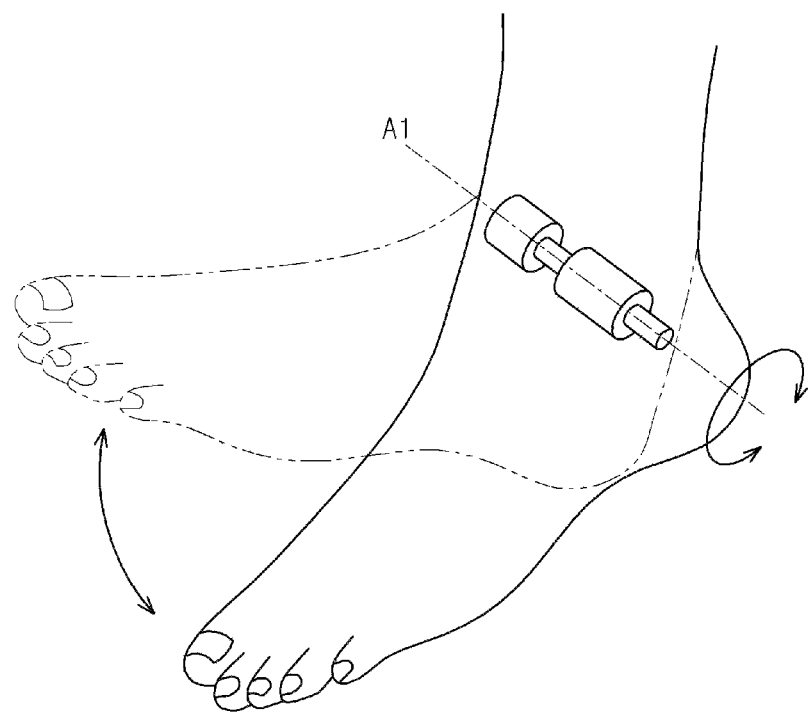
FIG. 2A is a diagram illustrating a state in which a user's foot is pivoted in a first direction with respect to an ankle joint.
Figure 2B:
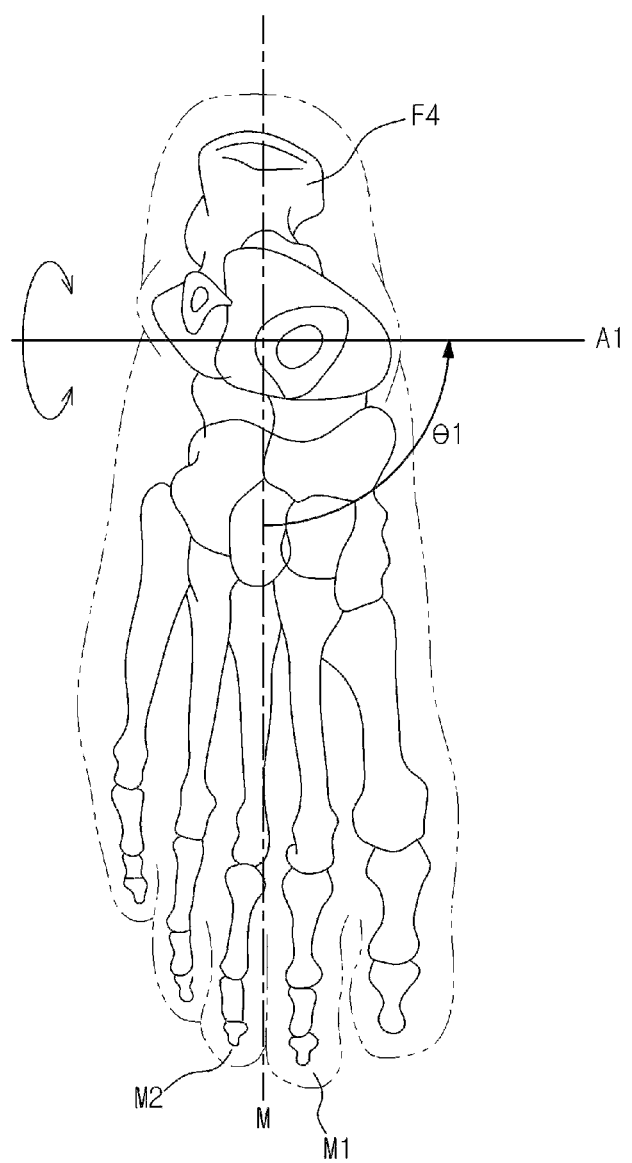
FIG. 2B is a diagram illustrating a first rotation axis of the user's ankle joint.
Figure 3A:
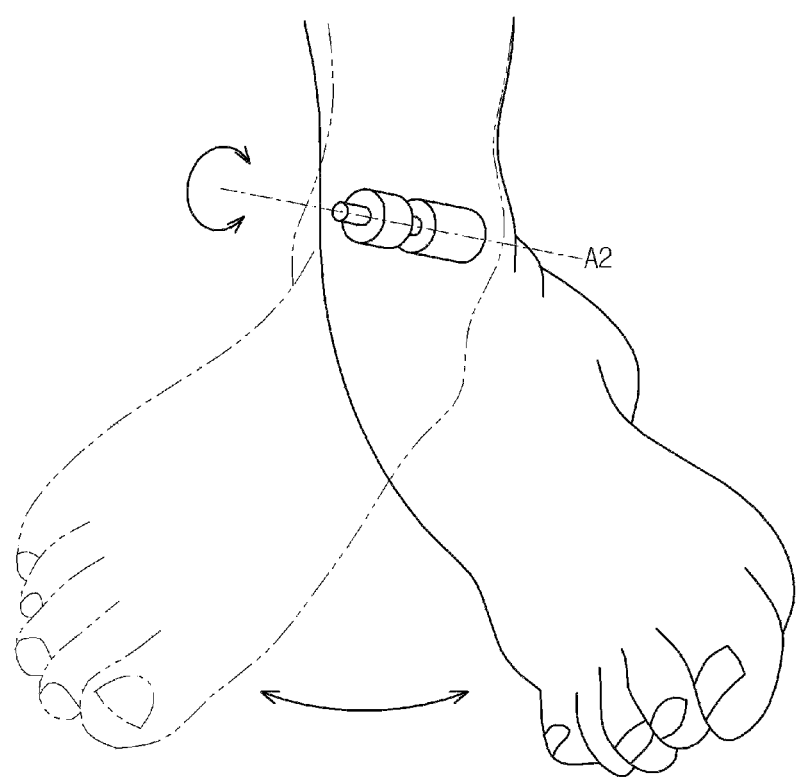
FIG. 3A is a diagram illustrating a state in which the user's foot is pivoted in a second direction with respect to the ankle joint.
Figure 3B:
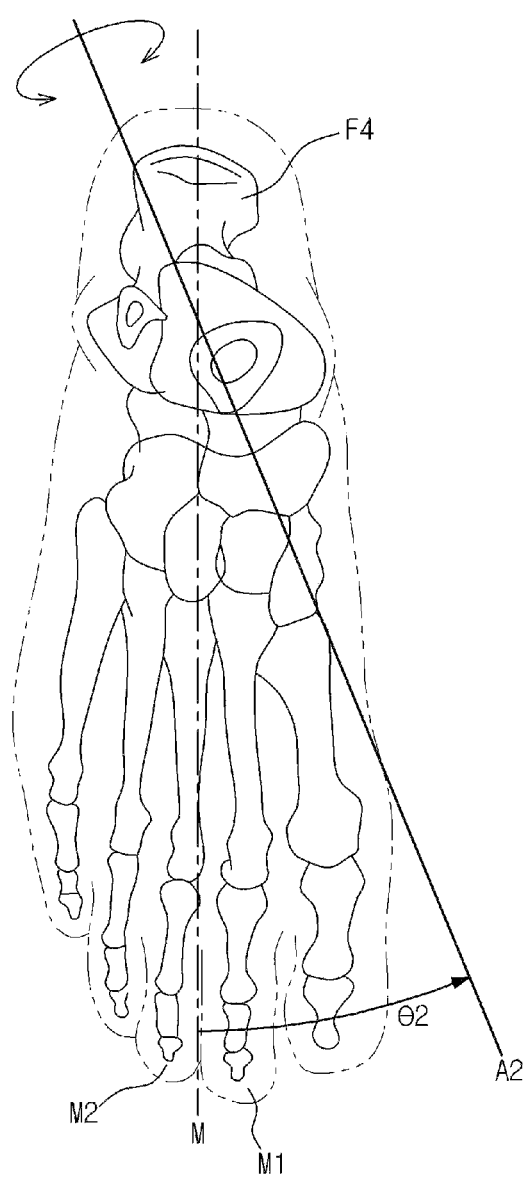
FIGS. 3B and 3C are diagrams illustrating a second rotation axis of the user's ankle joint.
Figure 3C:
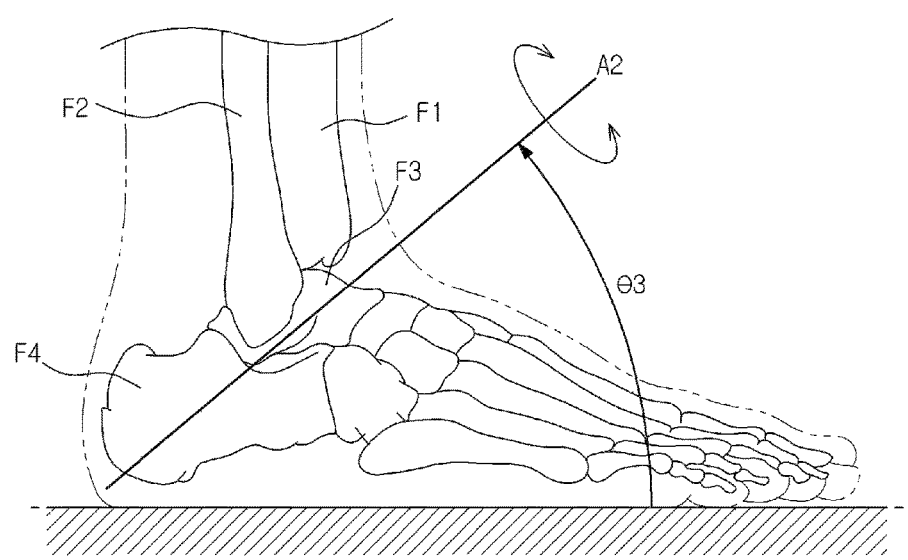

FIG. 2A is a diagram illustrating a state in which the user's foot is pivoted in a first direction with respect to the ankle joint. FIG. 2B is a diagram illustrating a first rotation axis of the user's ankle joint. FIG. 3A is a diagram illustrating a state in which the user's foot is pivoted in a second direction with respect to the ankle joint. FIGS. 3B and 3C are diagrams illustrating a second rotation axis of the user's ankle joint.

As illustrated in FIGS. 2A to 3C, the user's ankle joint may include a tibia (F1) connecting a calf portion and a foot, a fibula (F2) located behind the tibia (F1), and a talus (F3) connected to an end of the tibia (F1) and an end of the fibula (F2). The ankle joint may be pivoted around a first rotation axis A1 or a second rotation axis A2 according to a combination of movements of the tibia (F1), the fibula (F2), and the talus (F3).

The first rotation axis A1 may extend substantially perpendicular to an extending direction of the user's foot. The first rotation axis A1 may extend in a direction in which ankle bones located in left and right sides of the user's ankle joint portion are penetrated. An extending direction of the first rotation axis A1 may be referred herein as an x axis.

That is, the first rotation axis A1 may extend in the x axis direction. The user may pivot his or her foot around the first rotation axis A1 such that a toe faces upward or downward (plantar-flexion and dorsi-flexion).

When a line crossing between a second toe M1 from a big toe and a third toe M2 from the big toe and crossing a center of a calcaneus (F4) of the user is set as a reference line M, the first rotation axis A1 may extend to form an angle close to a right angle with respect to the reference line M. For example, when a top side of the user's foot is seen from the top, an angle ($\theta1$) between the reference line M and the first rotation axis A1 may be about 84°.

Hereinafter, a case in which the user's foot is pivoted around the first rotation axis A1 may mean that the user's foot is pivoted in the first direction.

The second rotation axis A2 may extend toward an upper front of the user. The second rotation axis A2 may extend to penetrate the user's ankle. The second rotation axis A2 may not cross the first rotation axis A1 in the user's ankle joint.

When the user's foot extends in the y axis, the second rotation axis A2 forms a desired (or, alternatively, a predetermined) angle with respect to the y axis, and may be located and extend in a plane formed by the y axis and the z axis. The user may pivot a foot around the second rotation axis A2. The user's foot may be pivoted (inversion and eversion) in a horizontal direction in which both ankle bones are located.

The second rotation axis A2 may form a desired (or, alternatively, a predetermined) angle with respect to the reference line M, and may extend to form a specific angle with respect to a floor surface with which a sole of the user's foot comes in contact. For example, when a top side of the user's foot is seen from the top, an angle ($\theta2$) between the second rotation axis A2 and the reference line M may be about 23°. When the user's leg is seen from the side, an angle ($\theta3$) between the second rotation axis A2 and the floor surface with which the sole of the user's foot comes in contact may be about 41°.

Hereinafter, a case in which the user's foot is pivoted around the second rotation axis A2 may mean that the user's foot is pivoted in the second direction.

The walking assistant robot may be mounted on an outer portion of the user's body, therefore, conventionally, an offset may occur between locations of the rotation axis of the ankle joint of the walking assistant robot and the second rotation axis of the user's ankle joint. Accordingly, when the user's foot rotates around the second rotation axis, in a conventional the walking assistant robot, the walking assistant robot may come apart from the user's body or an unnecessary load may be applied to the user's ankle joint.

In contrast, in some example embodiments, the walking assistant robot 1 may perform an operation similar to the second rotation axis of the user's ankle joint such that the walking assistant robot 1 may not come apart from the user's body and/or may not apply unnecessary load to the user's ankle joint.

Figure 4:
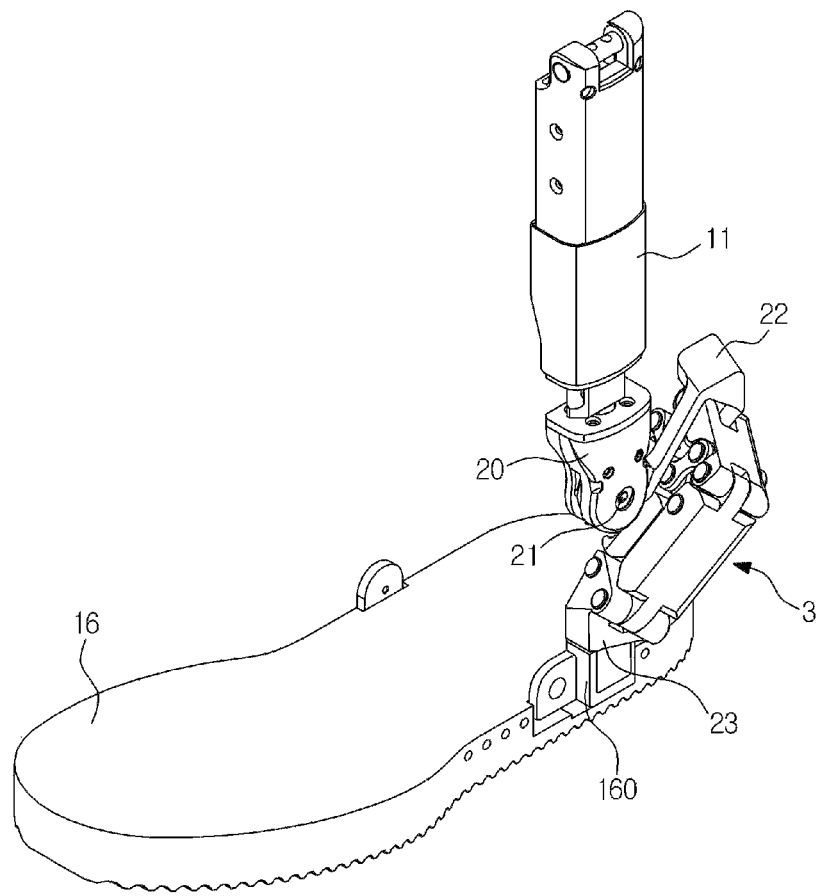
FIG. 4 is a perspective view illustrating an ankle joint included in a walking assistant robot according to some example embodiments.
Figure 5:
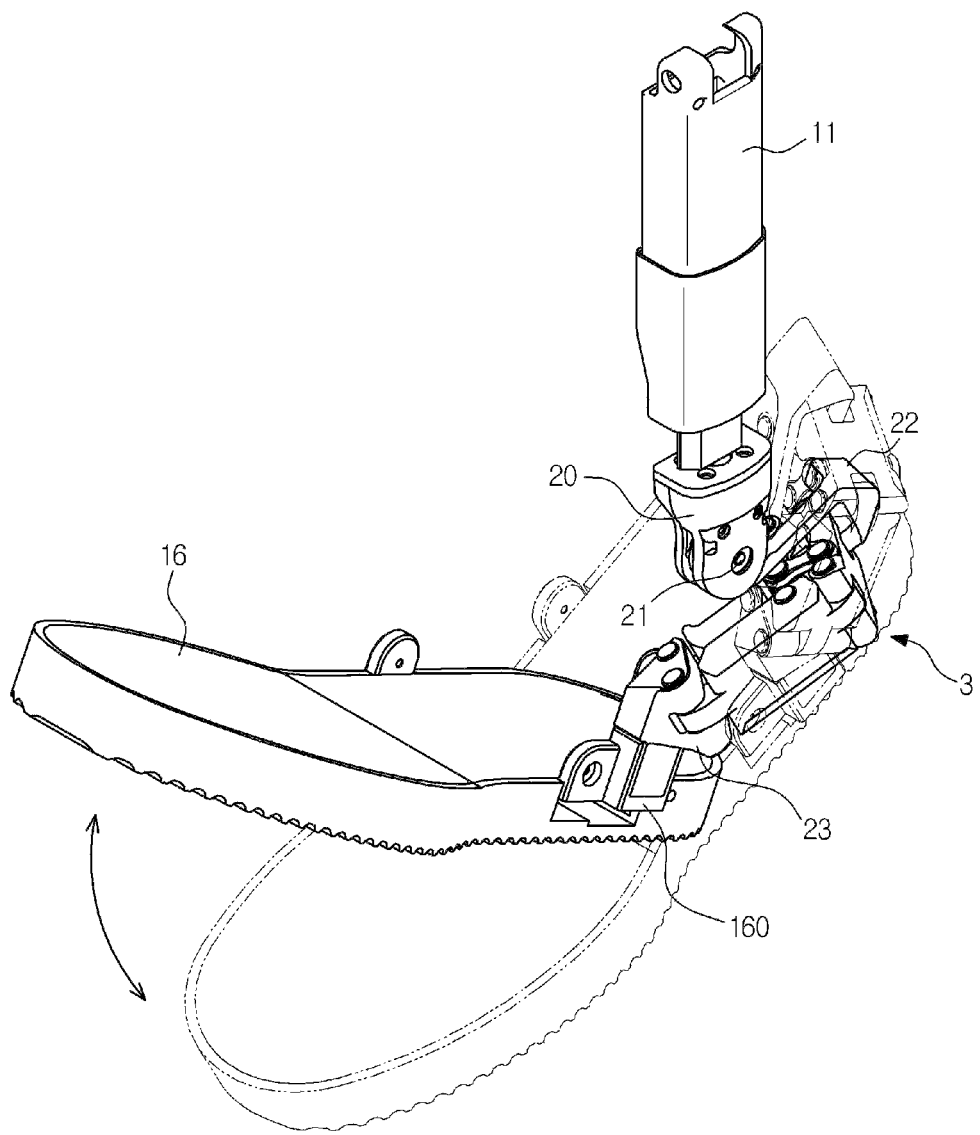
FIG. 5 is an exploded perspective view illustrating the ankle joint according to some example embodiments.

FIG. 4 is a perspective view illustrating the ankle joint included in the walking assistant robot according to some example embodiments. FIG. 5 is an exploded perspective view illustrating the ankle joint according to some example embodiments.

As illustrated in FIGS. 4 and 5, the ankle joint 2 included in the walking assistant robot 1 according to some example embodiments may include a first joint unit 20, a second joint unit 22, and a third joint unit 3. The first joint unit 20 may be connected to the second frame 11. The second joint unit 22 may be pivotably connected to the first joint unit 20. The third joint unit 3 may be pivotably connected to the second joint unit 22. The third joint unit 3 may be pivotably connected to the foot structure 16 by a connecting joint unit 23.

The first joint unit 20 may be mounted to the second frame 11. For example, one side of the first joint unit 20 may be fixed to the second frame 11.

At the other side of the first joint unit 20, the second joint unit 22 may be pivotably connected in the first direction to the first joint unit 20. For example, the second side of the first joint unit 20 and a first side of the second joint unit 22 may be pivotably connected by a rotation axis 21 penetrating the first joint unit 20 and the second joint unit 22. The second joint unit 22 may be pivoted around the rotation axis 21 in the first direction. The rotation axis 21 may extend in the x axis direction. The rotation axis 21 may support a load applied from the second frame 11.

At a second side of the second joint unit 22, the third joint unit 3 may be pivotably connected. The third joint unit 3 may be connected to the second joint unit 22 such that the third joint unit 3 may be pivoted in the second direction. The third joint unit 3 may extend in a y axis direction.

The connecting joint unit 23 may be connected to a second side of the third joint unit 3. Further, the connecting joint unit 23 may be connected to the foot structure 16. Accordingly, the second frame 11 may be connected to the foot structure 16 through the ankle joint 2.

The connecting joint unit 23 may be connected to the foot structure 16 through a connecting unit 160 provided in the foot structure 16. By adjusting a location in which the connecting joint unit 23 is mounted on the connecting unit 160, the walking assistant robot 1 may match locations of the first rotation axis A1 of the user's ankle joint with the rotation axis 21 of the ankle joint 2 of the walking assistant robot 1.

The third joint unit 3 may include a plurality of links. The plurality of links of the third joint unit 3 may be pivotably connected. A load applied to the third joint unit 3 may be supported by the plurality of links.

Figure 6:
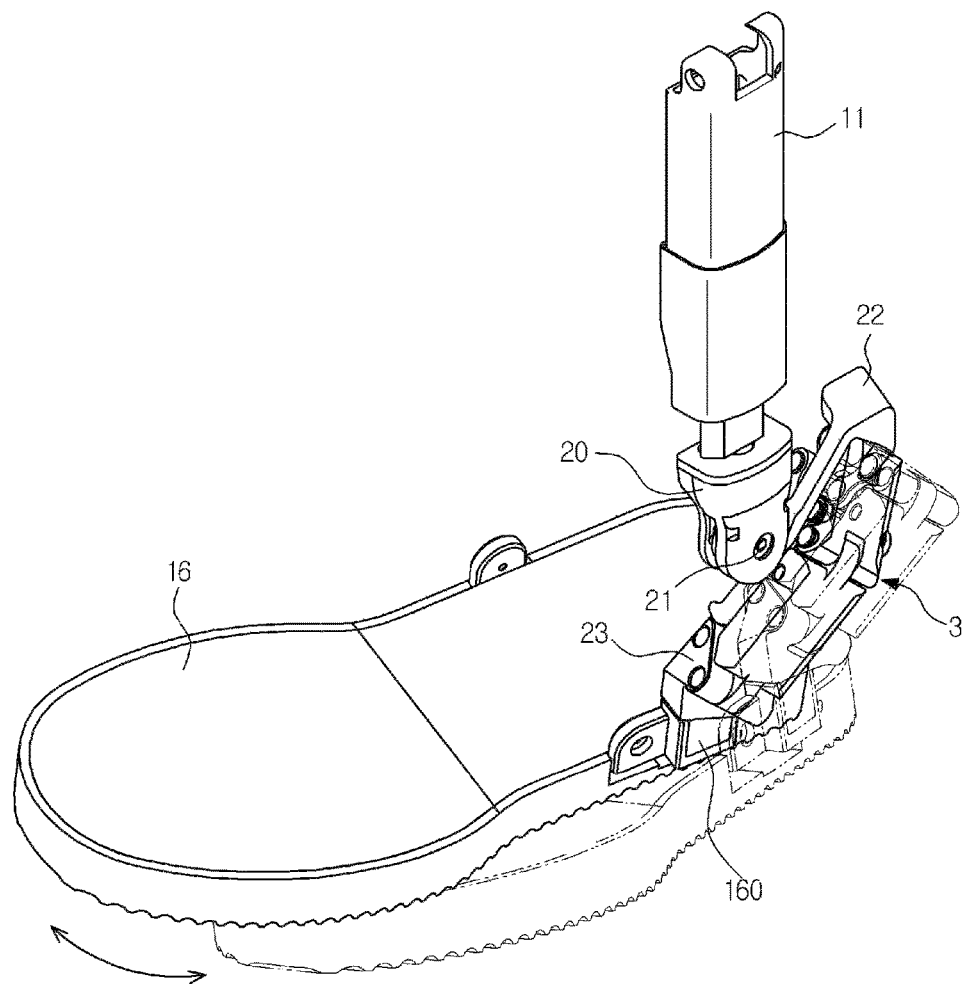
FIG. 6 is a diagram illustrating a pivot operation in a first direction of the ankle joint included in the walking assistant robot according to some example embodiments.
Figure 7:
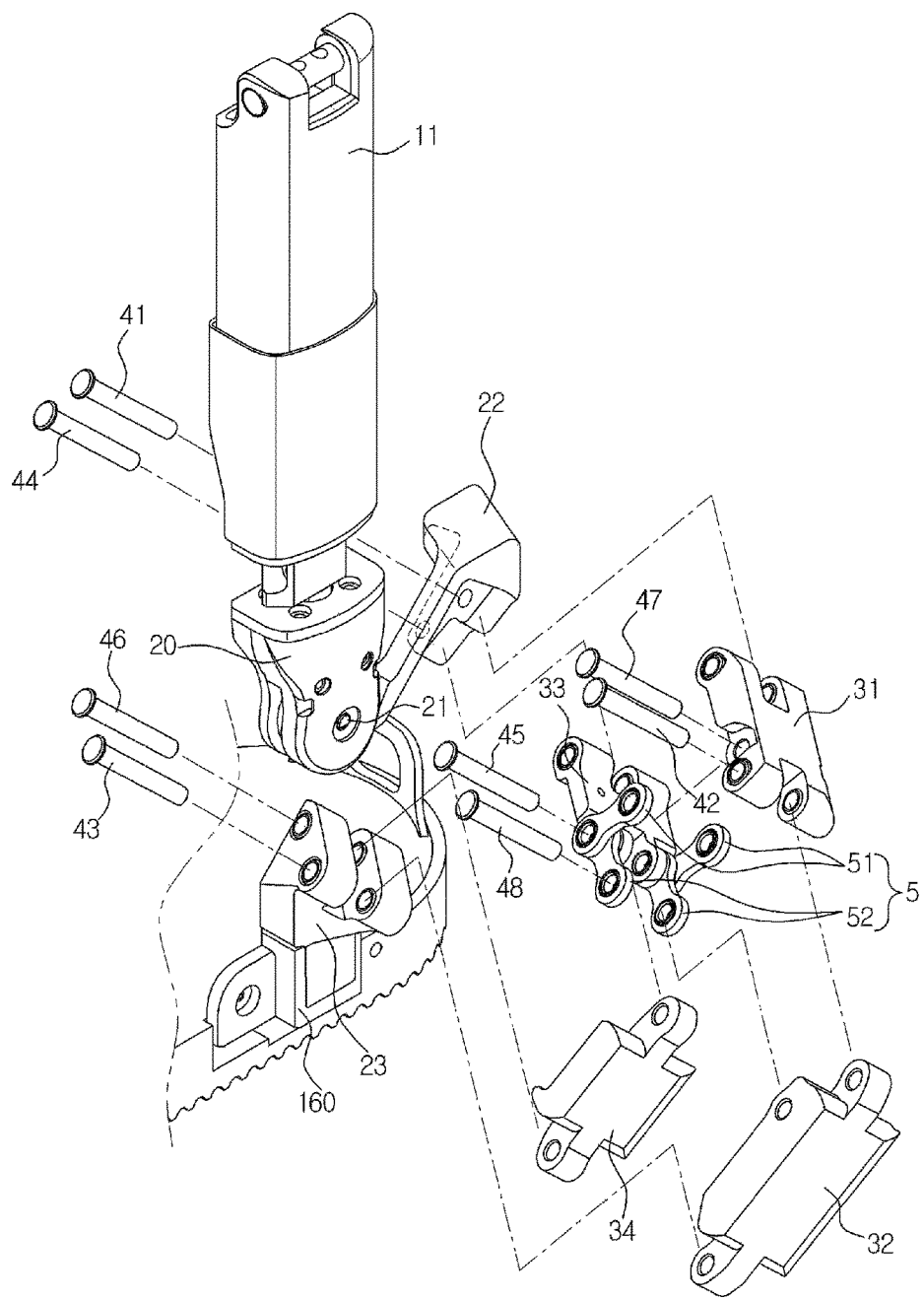
FIG. 7 is a diagram illustrating a pivot operation in a second direction of the ankle joint according to some example embodiments.

FIG. 6 is a diagram illustrating a pivot operation in the first direction of the ankle joint included in the walking assistant robot according to some example embodiments. FIG. 7 is a diagram illustrating a pivot operation in the second direction of the ankle joint according to some example embodiments.

Referring to FIGS. 6 and 7, the third joint unit 3 may include a first link 31, a second link 32, a third link 33, and a fourth link 34. The first link 31 and the third link 33 may be connected to the second side of the second joint unit 22. The second link 32 may be pivotably connected to the first link 31, and the fourth link 34 may be pivotably connected to the third link 33. The first link 31 and the third link 33 may be located so as to face each other. One surface of the first link 31 and one surface of the third link 33 may be parallel. The second link 32 and the fourth link 34 may face each other. One surface of the second link 32 and one surface of the fourth link 34 may be parallel.

Hereinafter, a structure in which the first link 31 and the second link 32 are connected may be called a first link unit (or, alternatively, front links), and a structure in which the third link 33 and the fourth link 34 are connected may be called a second link unit (or, alternatively, rear links). The first link unit and the second link unit may be pivoted in the second direction around a rotation axis inside the user's body wearing the walking assistant robot 1. The first link unit and the second link unit may be pivoted in the second direction similar to the user's ankle joint.

The third joint unit 3 may include a plurality of link axes pivotably connecting the joint units. For example, the third joint unit 3 may include a first link axis 41, a second link axis 42, a third link axis 43, a fourth link axis 44, a fifth link axis 45, and a sixth link axis 46.

The first link 31 may be pivotably connected to the second joint unit 22 by the first link axis 41 penetrating one side of the first link 31 and the other side of the second joint unit 22. The third link 33 may be pivotably connected to the second joint unit 22 by the fourth link axis 44 penetrating one side of the third link 33 and the other side of the second joint unit 22.

The first link 31 and the second link 32 may be pivotably connected by the second link axis 42. The second link axis 42 may penetrate the other side of the first link 31 and one side of the second link 32. The third link 33 and the fourth link 34 may be pivotably connected by the fifth link axis 45. The fifth link axis 45 may penetrate the other side of the third link 33 and one side of the fourth link 34.

The second link 32 and the connecting joint unit 23 may be pivotably connected by the third link axis 43. The third link axis 43 may penetrate the other side of the second link 32 and one side of the connecting joint unit 23. The fourth link 34 and the connecting joint unit 23 may be pivotably connected by the sixth link axis 46. The sixth link axis 46 may penetrate the other side of the fourth link 34 and one side of the connecting joint unit 23.

The third joint unit 3 may further include an assistant link 5. A distance between the first link unit and the second link unit may be constantly maintained by the assistant link 5. The assistant link 5 may include a first assistant link 51 and a second assistant link 52. The first assistant link 51 may connect the first link 31 and the fifth link axis 45. The second assistant link 52 may connect the second link 32 and the fifth link axis 45. A length of the first assistant link 51 may be the same as a length between the first link axis 41 and the fourth link axis 44. A length of the second assistant link 52 may be the same as a length between the third link axis 43 and the sixth link axis 46.

The first link 31 and the first assistant link 51 may be connected by a seventh link axis 47. In the first link 31, the seventh link axis 47 may be located between the first link axis 41 and the second link axis 42. The seventh link axis 47 may be provided between one end and the other end of the first link 31. The seventh link axis 47 may extend parallel to the first link axis 41 and the second link axis 42. The first assistant link 51 may connect the seventh link axis 47 and the fifth link axis 45. The seventh link axis 47 may be located such that a distance from the first link axis 41 to the seventh link axis 47 is the same as a distance from the fourth link axis 44 to the fifth link axis 45.

In the second link 32, an eighth link axis 48 located between the second link axis 42 and the third link axis 43 may be further installed. The eighth link axis 48 may extend parallel to the second link axis 42 and the third link axis 43. The eighth link axis 48 may be provided between one end and the other end of the second link 32. The second assistant link 52 may connect the eighth link axis 48 and the fifth link axis 45. The eighth link axis 48 may be located such that a distance from the eighth link axis 48 to the third link axis 43 is the same as a distance from the fifth link axis 45 to the sixth link axis 46.

A distance between the first link 31 and the second link unit may be constantly maintained by the first assistant link 51. A distance between the second link 32 and the second link unit may be constantly maintained by the second assistant link 52.

As illustrated in FIGS. 6 and 7, the ankle joint 2 of the walking assistant robot 1 according to some example embodiments may be pivoted in the first direction or the second direction. The ankle joint 2 of the walking assistant robot 1 may perform a pivot operation similar to a pivot operation around the first rotation axis A1 of the user's ankle joint and a pivot operation around the second rotation axis A2 thereof.

The ankle joint 2 of the walking assistant robot 1 may be pivoted around the rotation axis 21 (e.g. pivoted around the first direction). The rotation axis 21 may be on the same straight line as the first rotation axis A1 of the user's ankle joint. The ankle joint 2 of the walking assistant robot 1 may be pivoted in the first direction similar to a case in which the user's ankle joint is pivoted around the first rotation axis A1.

Further, the ankle joint 2 of the walking assistant robot 1 may be pivoted in the second direction. For example, the third joint unit 3 of the ankle joint 2 of the walking assistant robot 1 may be pivoted around the second rotation axis A2 of the user's ankle joint. The third joint unit 3 of the walking assistant robot 1 may be pivoted respect to the second joint unit 22 around the first link axis 41 and the fourth link axis 44. The third joint unit 3 may be pivoted respect to the connecting joint unit 23 around the third link axis 43 and the sixth link axis 46. Also, the third joint unit 3 may be pivoted around the second link axis 42 and the fifth link axis 45.

As described above, the third joint unit 3 includes the plurality of links and link axes, each link is pivoted around a link axis, and thereby the ankle joint 2 of the walking assistant robot 1 may be pivoted around the second rotation axis A2 of the actual ankle joint of the user wearing the walking assistant robot 1.

By enabling the ankle joint 2 of the walking assistant robot 1 to be pivoted around the second rotation axis A2 of the user's ankle joint, when the user wears the walking assistant robot 1 and pivots the ankle joint around the second rotation axis A2, the pivot may be performed while the walking assistant robot 1 comes in close contact with the user's body stably, and an unnecessary load may not be transmitted to the user's ankle joint.

Hereinafter, matching of a rotation center of the ankle joint 2 with the second rotation axis A2 of the user's ankle joint when the ankle joint 2 of the walking assistant robot 1 is pivoted in the second direction will be described.

Figure 8:
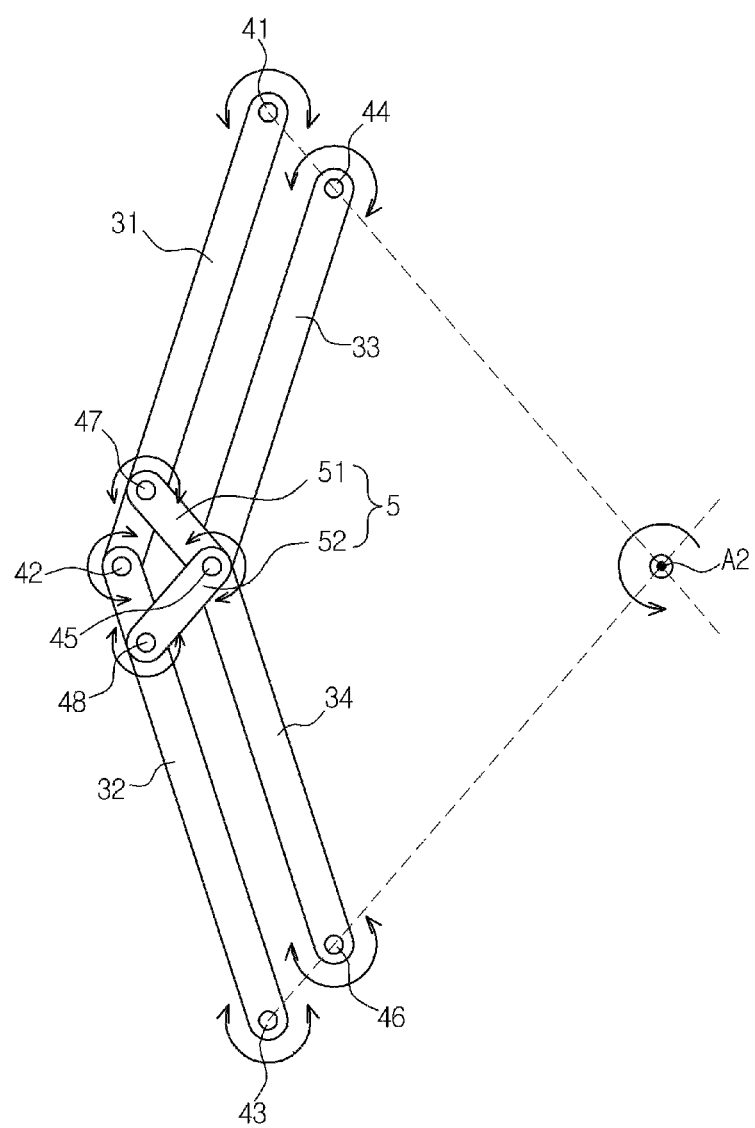
FIG. 8 is a conceptual diagram illustrating a part of the ankle joint according to some example embodiments.
Figure 9:
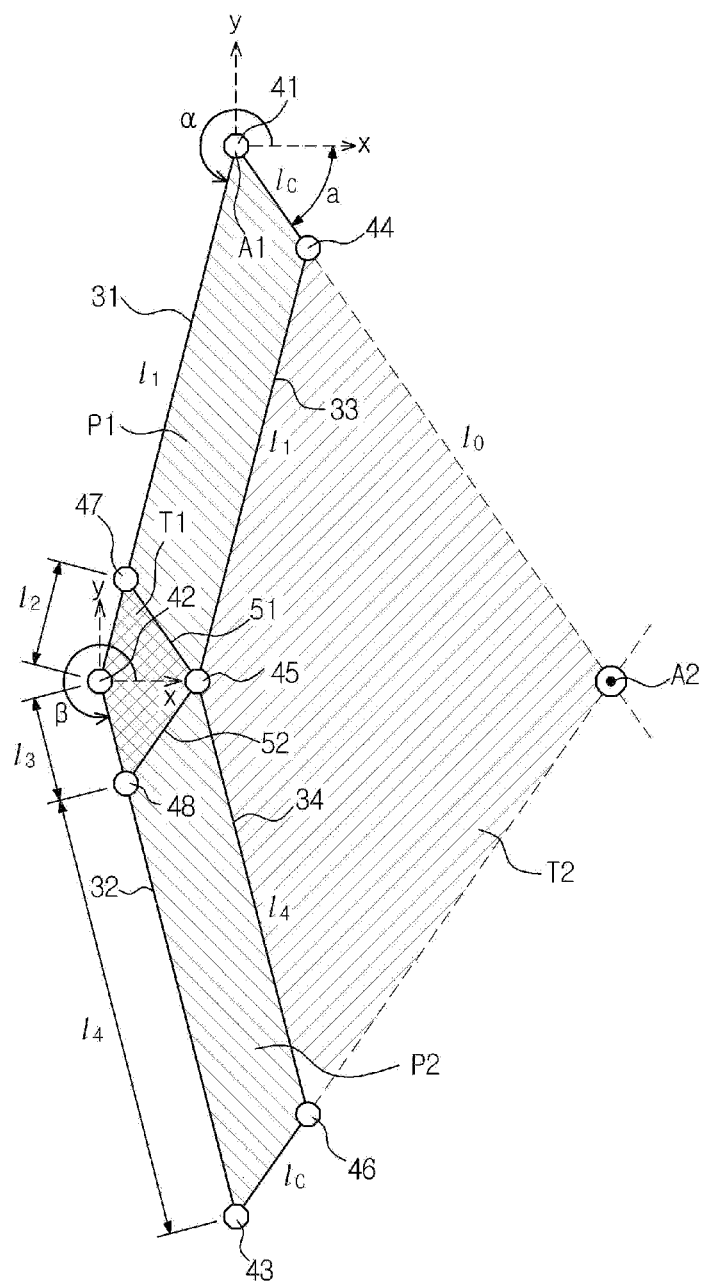
FIG. 9 is a diagram illustrating a relation between a pivot center axis and the ankle joint according to some example embodiments.

FIG. 8 is a conceptual diagram illustrating a part of the ankle joint according to some example embodiments. FIG. 9 is a diagram illustrating a relation between a pivot center axis and the ankle joint according to some example embodiments.

As illustrated in FIGS. 8 and 9, an ankle joint 2 of the walking assistant robot 1 according to some example embodiments may be pivoted around the second rotation axis A2 of the user's actual ankle joint. The ankle joint 2 is pivotably connected to the second joint unit 22 and includes the third joint unit 3 pivotably connected to the connecting joint unit 23. The third joint unit 3 includes a plurality of links, and the plurality of links may be pivoted around the plurality of link axes.

Hereinafter, pivoting of the ankle joint 2 of the walking assistant robot 1 around the second rotation axis A2 of the user's actual ankle joint will be described with reference to Equations 1-9. As discussed below, Equations 1-9 confirm that the ankle joint 2 of the walking assistant robot 1 may pivot around the second rotation axis A2 even when an angle formed by the first link 31 and the second link 32 or an angle formed by the third link 33 and the fourth link 34 is changed.

Therefore, the walking assistant robot 1 may not come apart from the user's body and/or may not apply unnecessary load to the user's ankle joint.

The first link axis 41 and the fourth link axis 44 may be located in the same straight line crossing the second rotation axis A2. Similarly, the third link axis 43 and the sixth link axis 46 may be located in the same straight line crossing the second rotation axis A2.

The first link 31, the first assistant link 51, the third link 33, and a straight line crossing the first link axis 41 and the fourth link axis 44 may form a first parallelogram P1. Similarly, the second link 32, the second assistant link 52, the fourth link 34, and a straight line crossing the third link axis 43 and the sixth link axis 46 form a second parallelogram P2. In this case, a figure (T1) formed by the seventh link axis 47, the fifth link axis 45, the eighth link axis 48, and the second link axis 42 may be similar to a figure (T2) formed by the fourth link axis 44, the second rotation axis A2, the sixth link axis 46, and the fifth link axis 45.

A distance from the fourth link axis 44 to the second rotation axis A2 is $l_0$. A distance from the first link axis 41 of the third joint unit 3 to the seventh link axis 47 is $l_1$. A distance from the fourth link axis 44 to the fifth link axis 45 is $l_1$, which is the same as the distance from the first link axis 41 to the seventh link axis 47.

A distance from the seventh link axis 47 to the second link axis 42 is $l_2$. A distance from the second link axis 42 to the eighth link axis 48 is $l_3$. A distance from the eighth link axis 48 to the third link axis 43 is $l_4$. A distance from the fifth link axis 45 to the sixth link axis 46 is $l_4$, which is the same as the distance from the eighth link axis 48 to the third link axis 43.

When a distance from the first link axis 41 to the fourth link axis 44 is $l_C$, a distance from the seventh link axis 47 to the fifth link axis 45, a distance from the third link axis 43 to the fifth link axis 45, and a distance from the third link axis 43 to the sixth link axis 46 may also be the distance $l_C$.

Since the figure (T1) formed by the seventh link axis 47, the fifth link axis 45, the eighth link axis 48, and the second link axis 42 is similar to the figure (T2) formed by the fourth link axis 44, the second rotation axis A2, the sixth link axis 46, and the fifth link axis 45, the relational expression may be expressed as:

$$l_0 : l_1 = l_c : l_2 \qquad \text{Equation 1}$$

When Equation 1 is solved for $l_0$, the following equation may be obtained:

$$l_0 = \frac{l_1 l_c}{l_2} \qquad \text{Equation 2}$$

When it is assumed that virtual x-y coordinates are in the first link axis 41, an angle between a line connecting the first link axis 41 and the fourth link axis 44 and an x axis is a. An angle formed by the first link 31 and the x axis is α. When it is assumed that x-y coordinates similar to the above are in the second link axis 42, an angle formed by the second link axis 42 and the x axis is β.

A location of the second rotation axis A2 may be represented by Equation 3:

$$\left(\left(l_c + \frac{l_1 l_c}{l_2}\right)\cos\alpha\right)i - \left(\left(l_c + \frac{l_1 l_c}{l_2}\right)\sin\alpha\right)j \qquad \text{Equation 3}$$

A location of the third link axis 43 may be represented by Equation 4:

$$((l_1+l_2)\cos\alpha + (l_3+l_4)\cos\beta)i + ((l_1+l_2)\sin\alpha + (l_3+l_4)\sin\beta)j \qquad \text{Equation 4}$$

A location of the sixth link axis 46 may be represented by Equation 5:

$$(l_c\cos\alpha + l_1\cos\alpha + l_4\cos\beta)i + (-l_c\sin\alpha + l_1\sin\alpha + l_4\sin\beta)j \qquad \text{Equation 5}$$

A straight line crossing the second rotation axis A2, the third link axis 43, and the sixth link axis 46 may have a relational expression of $y = C(x-x_0) + y_0$. When Equations 3-5 are substituted into the relational expression, $y = C(x-x_0) + y_0$, may be summarized as Equations 6-8.

$$C = \frac{-l_c\sin\alpha - l_2\sin\alpha - l_3\sin\beta}{l_c\cos\alpha - l_2\cos\alpha - l_3\cos\beta} \qquad \text{Equation 6}$$

$$x_0 = l_c\cos\alpha + l_1\cos\alpha + l_4\cos\beta \qquad \text{Equation 7}$$

$$y_0 = -l_c\sin\alpha + l_1\sin\alpha + l_4\sin\beta \qquad \text{Equation 8}$$

Further, when Equations 6-8 are substituted into the relational expression of $y = C(x-x_0) + y_0$, and the location of the second rotation axis A2 described by Equation 3 is substituted for values of x and y, the relational expression may be summarized as Equation 9:

$$(l_2 l_4 - l_1 l_3)\sin\alpha \cos\beta + (l_1 l_3 - l_2 l_4)\sin\beta \cos\alpha = 0 \qquad \text{Equation 9}$$

When Equation 2 is substituted into the relational expression of Equation 9, it may be confirmed that the same second rotation axis A2 is always obtained since both left and right sides of the relational expression of Equation 9 are zero regardless of α and β. That is, the ankle joint 2 of the walking assistant robot 1 may be always pivoted around the second rotation axis A2 of the user's actual ankle joint.

The first link 31, the first assistant link 51, the third link 33, and a straight line crossing the first link axis 41 and the fourth link axis 44 form the first parallelogram P1. The second link 32, the second assistant link 52, the fourth link 34, and a straight line crossing the third link axis 43 and the sixth link axis 46 form the second parallelogram P2. Accordingly, the ankle joint 2 may always pivot around the second rotation axis A2. Even when an angle formed by the first link and the second link or an angle formed by the third link and the fourth link is changed, the third joint unit 3 may be pivoted around the second rotation axis A2. Therefore, the ankle joint 2 of the walking assistant robot 1 may be pivoted in the second direction similar to the user's actual ankle joint.

As described above, since the ankle joint 2 of the walking assistant robot 1 is pivotable in the first direction or the second direction similar to the user's actual ankle joint, when the user wearing the walking assistant robot 1 pivots the ankle joint, it is possible to prevent the load from being transmitted to the user's ankle or a location of the frame of the walking assistant robot 1 with which the user's body comes in contact from being changed.

According to some example embodiments, a joint assembly operates similar to a user's actual ankle joint. An ankle joint included in a walking assistant robot 1 may support a load of the user.

Although a few example embodiments have been shown and described, it would be appreciated by those skilled in the art that changes may be made to these example embodi-

What is claimed is:

1. A joint assembly configured to connect a frame of a walk assistance robot and a foot structure of the walk assistance robot, the walk assistance robot configured to mount on a body of a user, the joint assembly comprising:
   a first joint mounted on the frame;
   a second joint pivotably and directly connected to the first joint, the second joint being pivotable in a first direction; and
   a third joint connected to the second joint, the third joint being pivotable in a second direction, the second direction being a direction that is not parallel to the first direction, the third joint including,
      front links including a first link and a second link, the first link being pivotably connected to the frame and the second link having one side pivotably and directly connected to the first link and another side pivotably connected to the foot structure,
      rear links including a third link and a fourth link, the third link being pivotably connected to the frame such that the third link is parallel to the first link and the fourth link having one side pivotably and directly connected to the third link and the other side pivotably connected to the foot structure such that the fourth link is parallel to the second link, and
      an assistant link configured to maintain a distance between the front links and the rear links, wherein
      the front links and the rear links are pivotable around a same rotation axis located outside the joint assembly,
      the rotation axis is fixed regardless of the rotation of the front links and the rear links,
      the assistant link includes a first assistant link and a second assistant link, the first assistant link configured to connect the first link and the rear links and the second assistant link configured to connect the second link and the rear links,
      one side of the first assistant link is mounted on a link axis provided between ends of the first link, and another side of the first assistant link is mounted on a link axis connecting the third link and the fourth link, and
      the second joint is configured to articulate in the first direction such that a foot of the user can pivot upward and downward to perform dorsi-flexion and plantar-flexion, respectively.

2. The joint assembly according to claim 1, wherein the third joint is configured to articulate in the second direction such that a foot of the user can pivot in a horizontal direction to perform inversion and eversion.

3. The joint assembly according to claim 1, wherein, one side of the second assistant link is mounted on a link axis provided between ends of the second link, and another side of the second assistant link is mounted on a link axis connecting the third link and the fourth link.

4. The joint assembly according to claim 1, wherein a distance between a link axis connecting the first link and the frame and a link axis connecting the first link and the first assistant link is equal to a distance between a link axis connecting the third link and the frame and a link axis connecting the third link and the fourth link.

5. The joint assembly according to claim 1, wherein a distance between a link axis connecting the second assistant link and the second link and a link axis connecting the second link and the foot structure is equal to a distance between a link axis connecting the third link and the fourth link and a link axis connecting the fourth link and the foot structure.

6. The joint assembly according to claim 1, wherein
   the first link, the first assistant link, and the third link form a shape of a parallelogram, and
   the second link, the second assistant link, and the fourth link form a shape of a parallelogram.

7. The joint assembly according to claim 1, wherein
   the front links and the rear links are pivotably connected to the second joint, and
   the second joint is pivotable in the first direction and the front links and the rear links are pivotable in the second direction.

8. The joint assembly according to claim 1, wherein the front links and the rear links are pivotably connected to a connecting joint mounted on the foot structure.

9. The joint assembly according to claim 8, wherein
   the foot structure includes a connector on which the connecting joint is mounted, and
   the connector and the connecting joint are configured to move up and down.

* * * * *

UNITED STATES PATENT AND TRADEMARK OFFICE
CERTIFICATE OF CORRECTION

PATENT NO. : 10,219,968 B2  
APPLICATION NO. : 14/592694  
DATED : March 5, 2019  
INVENTOR(S) : Jong Won Lee et al.

Page 1 of 1

It is certified that error appears in the above-identified patent and that said Letters Patent is hereby corrected as shown below:

On the Title Page

Item (30) should read:  
(30) Jan. 16, 2014    (KR).....10-2014-0005453

Signed and Sealed this  
Fourteenth Day of April, 2020

Andrei Iancu  
*Director of the United States Patent and Trademark Office*